United States Patent
Meythaler et al.

(10) Patent No.: US 7,354,954 B1
(45) Date of Patent: Apr. 8, 2008

(54) USE OF GABA AGONISTS FOR TREATMENT OF SPASTIC DISORDERS, CONVULSIONS, AND EPILEPSY

(76) Inventors: Jay M. Meythaler, 1811 Catala Rd., Birmingham, AL (US) 35216; Jean Peduzzi, 240 Camellia Rd., Chelsea, AL (US) 35043

( * ) Notice: Subject to any disclaimer, the term of this patent is extended or adjusted under 35 U.S.C. 154(b) by 0 days.

(21) Appl. No.: 10/049,328

(22) PCT Filed: Aug. 10, 2000

(86) PCT No.: PCT/US00/21886

§ 371 (c)(1),
(2), (4) Date: May 15, 2002

(87) PCT Pub. No.: WO01/10432

PCT Pub. Date: Feb. 15, 2001

(51) Int. Cl.
*A61K 31/197* (2006.01)
(52) U.S. Cl. ............. 514/561; 514/563; 514/626; 514/641
(58) Field of Classification Search ....... 514/563, 514/641
See application file for complete search history.

(56) References Cited

U.S. PATENT DOCUMENTS

| | | | | |
|---|---|---|---|---|
| 4,563,478 A | | 1/1986 | Curti et al. | 614/561 |
| 5,474,547 A | * | 12/1995 | Aebischer et al. | 604/891.1 |
| 5,832,932 A | | 11/1998 | Elsberry et al. | 128/898 |

OTHER PUBLICATIONS

Hsu, C.Y. et al., "Cell-Mediated Injury," 106:1433-1444.
Juurlink, B. et al., "Review of Oxidative Stress in Brain and Spinal Cord Injury: Suggestions for Pharmacological and Nutritional Management Strategies," The Journal of Spinal Cord Medicine, 21:309-334;1998.
Smith, D. H. et al., "Traumatic Brian Injury and Excitatory Amino Acids," 107:1445-1458.
Akman et al. "Intrathecal baclofen: does tolerance occur?" Paraplegia 31 (1993) 516-520.
Bergmann. "Progabide: A New GABA-Mimetic Agent in Clinical Use" Clinical Neuropharmacology, vol. 8, No. 1, pp. 13-26 (1985).
Coffey et al. "Intrathecal baclofen for intractable spasticity of spinal origin: results of a long term multicenter study" J. Neurosurg., vol. 78, pp. 226-232 (Feb. 1993).
Klockgether et al. "Myorelaxant effect after intrathecal injection of antispastic drugs in rats" Neuroscience Letters, 97 (1989) 221-226.
Knutsson et al. "Plasma and Cerebrospinal Fluid Levels of Baclofen (Lioresal) at Optimal Therapeutic Responses in Spastic Paresis" Journal of the Neurological Sciences, 23: 473-484 (1974).
Kroin et al. "Reduced Spinal Reflexes Following Intrathecal Baclofen in the Rabbit" Exp. Brain Res. 54: 191-194 (1984).
Lazorthes et al. "Chronic intrathecal baclofen administration for control of severe spasticity" J. Neurosurg. 72: 393-402 (1990).
Meythaler et al. "Prospective assessment of continuous intrathecal infusion of baclofen for spasticity caused by acquired brain injury: a preliminary report" J. Neurosurg. 87: 415-419 (1997).
Penn et al. "Intrathecal Baclofen for Severe Spinal Spasticity" The New England Journal of Medicine, vol. 320, No. 23, pp. 1517-1521 (Jun. 8, 1989).
Sandyk et al. "Baclofen-Induced Memory Impairment" Clinical Neuropharmacology, vol. 8, No. 3, pp. 294-295 (1985).
Wilson et al. "Baclofen is Antinociceptive in the Spinal Intrathecal Space of Animals" European Journal of Pharmacology 51: 323-330 (1978).
Young et al. "Drug Therapy—Spasticity (First of Two Parts)" The New England Journal of Medicine, vol. 304, No. 1, pp. 28-33 (Jan. 1, 1981).
Young et al. "Drug Therapy—Spasticity (Second of Two Parts)" The New England Journal of Medicine, vol. 304, No. 2, pp. 96-99 (Jan. 8, 1981).
Kaplan et al. New Anticonvulsants: Schiff Bases of gamma-Aminobutyric Acid and gamma-Aminobutyramide J. Med. Chem. 23:702-704 (1980).

* cited by examiner

*Primary Examiner*—Ardin H. Marschel
*Assistant Examiner*—Donna Jagoe
(74) *Attorney, Agent, or Firm*—Gifford, Krass, Sprinkle et al.

(57) ABSTRACT

According to the subject invention, there is disclosed a method for treating a patient/subject having a spastic disorder, a convulsive disorder, pain or epilepsy which includes administering to the subject having any one of these conditions a therapeutically effective amount of the compound gamma-aminobutyramide, analogs, substituted forms, derivatives, the pharmaceutically acceptable salts, esters, amides, and prodrugs thereof, or compounds which yield gamma-aminobutyramide as an intermediate, a metabolite, or a by-product.

17 Claims, 1 Drawing Sheet

USE OF GABA AGONISTS FOR TREATMENT OF SPASTIC DISORDERS, CONVULSIONS, AND EPILEPSY

FIELD OF THE INVENTION

The subject invention relates to the use of gamma-aminobutyric acid (GABA) analogs and, more specifically, to the treatment of spastic disorders, convulsions, and epilepsy by administering gamma-aminobutyramide and/or any drug or compound which is broken down to yield gamma-aminobutyramide, such as by metabolism in a subject administered the drug or compound or by solubilization of a drug or compound to yield gamma-aminobutyrate.

BACKGROUND OF THE INVENTION

By way of background, gamma-aminobutyric acid (GABA) and glutamic acid are major neurotransmitters which are involved in the regulation of brain neuronal activity. GABA is a major inhibitory neurotransmitter in the mammalian central nervous system. Meythaler et al., *Arch. Phys. Med. Rehabil.* 1999; 80: 13-9. Imbalances in the levels of GABA in the central nervous system can lead to conditions such as spastic disorders, convulsions, and epileptic seizures. As described in U.S. Pat. No. 5,710,304, when GABA levels rise in the brain during convulsions, seizures terminate.

GABA is present in an estimated 60 to 70% of all the synapses in the brain (*Med. Sci. Bull.* 1997; 20(5)). There are two types of receptors, GABA-A and GABA-B. The B receptors appear to be involved in spasticity (Meythaler 1996, Young 1981), while the A receptors appear to be involved in the control of epilepsy (*Med. Sci. Bull.* 1997; 20(5)). In fact, GABA-A antagonists cause convulsions in animal models (*Med. Sci. Bull.* 1997; 20(5)) as well as spasticity.

Because of the inhibitory activity of GABA and its effect on convulsive states and other motor dysfunctions, the administration of GABA to subjects to increase the GABA activity in the brain has been tried. Because it is difficult to develop and administer a GABA compound which is able to cross the blood brain barrier utilizing systemic administration of GABA compounds, different approaches have been undertaken including making GABA lipophilic by conversion to hydrophobic GABA amides or GABA esters, and by administering activators of L-glutamic acid decarboxylase (GAD) whose levels vary in parallel with increases or decreases of brain GABA concentration which have been reported to increase GABA levels.

U.S. Pat. No. 4,094,992 to Kaplan et al. discloses benzylidene derivatives which are useful in the treatment of epilepsy and U.S. Pat. No. 4,361,583 to Kaplan discloses the use of the benzylidene derivatives for use in the treatment of pain. This class of drugs are strong GABA agonists which are effective on both GABA-B and GABA-A receptors.

One specific benzylidene derivative disclosed in U.S. Pat. No. 4,094,992 has the chemical structure 4-[[(4-chlorophenyl)-(5-fluoro-2-hydroxyphenyl)methylene]amino]butanamide and is more commonly known as PROGABIDE (SL 76002). PROGABIDE does not appear to cause motor weakness in therapeutic dosages to control spasticity and does not appear to significantly affect cognition. There is some suggestion that progabide is an anti-epileptic agent and that it is also neuroprotective. Polasek et al., *Epilepsy Research* 1996; 25:177-84; Kulinskii et al., *Eksperimntalnaia I Klinicheskaia Farmakologiia* 1997; 60:56-8.

As discussed above, there are inherent difficulties in the effective administration of GABA and/or its derivatives to a subject in order to increase brain GABA levels. One of the most pronounced drawbacks of GABA administration is that it does not easily cross the blood brain barrier and, accordingly, does not enter the central nervous system after oral or parenteral administration. The benzylidene derivatives disclosed in the Kaplan et al. patent are considered to be "GABA-mimetic" and are capable of penetrating directly into the brain when administered by oral, endo-rectal, or parenteral routes.

It has been found, however, that, in the brain, when GABA agonists are delivered orally, they may cause some supraspinal activity which may contribute to clinical side effects. For example, for the GABA-B agonist baclofen, it has been found that following oral delivery of the drug that many patients experience central nervous system side effects such as drowsiness, confusion, or memory or attentional problems at the dosages required to reduce spasticity. Young et al., *New Eng. J. Med.,* 1981; 304:28-33; Young et al., *New Eng. J. Med.,* 1981; 304:96-99; Lazorthes et al., *J. Neurosurg.* 1990; 72:393-402; Sandy et al., *Clin. Neuropharm.* 1985; 8:294-295. Other central nervous system side effects of GABA agonists have included hallucinations, ataxia and memory impairments. Sandy et al., *Clin. Neuropharm.* 1985; 8:294-295; Hattab, *Spasticity, Disordered Motor Control,* 1980; Roy et al., *Paraplegia* 1986; 24:318-321. Additionally, the sudden withdrawal of orally delivered GABA compounds may itself lead to seizures and hallucinations. Terrence et al., *Arch. Neurol.* 1981; 38:588-589.

The side effects noted above with the systemic administration of GABA agonists can be largely averted by utilizing intrathecal drug delivery since intrathecal delivery of GABA compounds to the lumbar or mid-thoracic spinal intrathecal space concentrates the medication in the lower area of the spinal cord cerebrospinal fluid at much higher levels than those attainable via the oral route of administration (Meythaler, McCary, Hadley 1996). Typically, the type of delivery system for intrathecal therapy consists of a subcutaneously placed pump having a reservoir which is attached to an intraspinal catheter. This drug delivery methodology concentrates the medication within the spinal subarachnoid space and the thoracolumbar and sacral spinal regions at a much higher level than that attainable via the oral route of administration. Meythaler et al., *J. NeuroSurgery* 1997; 87:415-9. From the subarachnoid space, the cerebrospinal fluid then flows to the arachnoid villi for reabsorption thereby avoiding a significant part of the cerebral hemispheres. Meythaler et al., *Arch. Phys. Med. Rehabil.* 1996; 77:461-466. Only low levels of the medication have the potential to reach the brainstem or cerebrum as studies have demonstrated the lumbar-to-cisternal drug cerebrospinal fluid (CSF) drug concentration gradient is 4.1:1. Kroin et al., *Parenteral Drug Therapy in Spasticity and Parkinsons Disease* 1991, pp. 73-83. By utilizing intrathecal drug delivery, the cognitive side effects of oral drug delivery, such as drowsiness and lethargy, can be avoided. Coffey et al., *J. Neurosurg.* 1993; 78:226-232; Penn et al., *N. Engl. J. Med.* 1989; 320:1517-1522; Knuttson et al., *J. Neurol. Sci.* 1974; 23:473-484. Furthermore, intraventricular delivery does the same for the periventricular area or region of the brain.

Preclinical animal studies in a canine model of the GABA-B agonist, baclofen (2000 μg/d for 28 days), intrathecally through a subcutaneously implanted pump demonstrated no deleterious histopathology in the studied animals. (Sabbe 1993). Initial work examining the use of GABA agonists both by systemic delivery and by intrathecal delivery in animal models revealed that baclofen produced a dose dependent analgesia (Bergmann; *Clin. Neuropharcol.* 1985; 8:13-26; Wilson et al., *European J. Pharmacol.* 1978; 51:323-330) and a reduction in motor tone in normal (Bergmann; *Clin. Neuropharcol.* 1985; 8:13-26; Wilson et al., *European J. Pharmacol.* 1978; 51:323-330; Kroin et al., *Exp. Brain Research* 1984; 54:191-194) and genetically spastic animals (Klockgether et al., *Neurosci. Lett.* 1989; 97:221-226).

Based on electrophysiology and the above-discussed preclinical studies, the mechanism of the anti-spasticity associated with intrathecally delivered baclofen is believed to be due to the hyperpolarization of motor horn cells. After the development or onset of upper motor neuron lesions, a variety of long term changes are observed in the brain. Mendell, *Physiological Reviews* 1984; 64(1):260-324. Among these changes, there is an increase in Ia motor unit activity. Wilson et al., *European J. Pharmacol.* 1978; 51:323-330. In humans, while motor horn cells show little change in recurrent inhibition after spinal injury, there is a loss of regulation of Renshaw cell inhibition (Katz et al., *Brain* 1982 March, 105(Pt 1): 103-24) and an increased motor neuron excitability (Shemesh et al., *Paraplegia* 1977 Nov., 15(3):238-44).

Despite the initial success of the intrathecally delivered GABA agonist baclofen in treating the dystonia/spasticity associated with spinal disorders (Meythaler et al., *Arch. Phys. Med. Rehabil.* 1999; 80:13-9; Penn et al., *N. Engl. J. Med.* 1989; 320:1517-1522; Muller et al., *Local-spinal therapy of spasticity* 1988, pp. 223-226), there is still little interest in treating cerebral disorders with intrathecally administered GABA agonists. This lack of interest appears to stem from the lack of success with oral medications in the treatment of dystonia/spasticity resulting from traumatic brain injury (Katz, *Phys. Med. Clin. N. Am.* 1992; 3:319-335; Mann, *J. Neuro. Rehab.* 1991; 5:51-54; Katz, *Am. J. Phys. Med. Rehabil.* 1988; 67:108-116). However, there were indications from some reports that this may be a useful methodology to improve the functional outcome of traumatically brain injured patients. Meythaler et al., *J. Neuro-Surgery* 1997; 87:415-9; Meythaler et al., *Arch. Phys. Med. Rehabil.* 1996; 77:461-466. Once clinical trials utilizing programmable infusion pump systems to intrathecally deliver baclofen for the management of dystonia/spasticity in traumatic brain injury were finally initiated, the results were favorable. Meythaler et al., *J. NeuroSurgery* 1997; 87:415-9; Akman et al., *Paraplegia* 1993; 31:516-20. However, not all patients have had a significant sustained response with intrathecally administered baclofen (Meythaler et al., *Arch. Phys. Med. Rehabil.* 1999; 80:13-9), which may be related to its effect only on GABA-B receptors.

Gamma-aminobutyramide appears to bind to both GABA-A and B receptors and it is an excellent candidate for use intrathecally as it is soluble in water and relatively stable for long periods of time. It is able to penetrate from the CNS into the central nervous system. Both the temporal horns and the frontal lobes of the brain are contiguous to the cerebral ventricles which contain CSF. 70% of all seizures are found to be originating in these areas by EEG monitoring. Consequently, intraventricular delivery of gamma-aminobutyramide should be useful in alleviating seizures.

Accordingly, the use of gamma-aminobutyramide, a solubility product of PROGABIDE, which is an agonist of both GABA-B receptors and GABA-A receptors, for the treatment of dystonia/spasticity in traumatically brain injured individuals is likely to have a more significant effect. This outcome is indicated by research which indicates that systemically delivered diazepam, a GABA-A receptor agonist, also has profound effects on dystonia and spasticity. Meythaler et al., *Perspectives in Neurosurg.* 1996; 7(2):99-107. The intrathecal and/or intraventricular administration of gamma-aminobutyramide directly into the cerebrospinal fluid will significantly limit its systemic toxicity due to the low doses delivered and to the small amount of the chemical or its metabolites that will reach the liver from that reabsorbed from the reabsorbed CSF at the arachnoid villi. Additionally, it has been speculated that gamma-aminobutyramide could be useful to reduce spasticity, dystonia, and have effects as an anti-convulsant if its toxicity and delivery issues could be solved. Kaplan et al., *J. Med. Chem.,* 1980; 23:702-4. Finally, GABA agonists have been used for the treatment of neurogenic pain (Baclonja M, et al., Gabapentin for the symptomatic treatment of painful neuropathy in patients with diabetes mellitus. *JAMA,* 1998, 280.1831-6). GABA-B agonists given intrathecally may also aid in the treatment of vaso-motor disorders related to upper motor neuron injury or illness (Rode G., et al., Regression of vasomotor disorders under intrathecal baclofen in a base report. *Spinal Cord,* 1999; 37:370-2).

There is some evidence that the movement disorder tardive dyskinesia may respond to GABA agonists. It is felt that the receptors that are targeted are GABA receptors near the globus pallidus and corpus callosum (Soares et al., *Cochran Library*, Issue 1 1999). Both of these areas are contiguous to the flow of the CSF from the lateral ventricles and down through the third ventricle. While GABA agonists may have been somewhat effective, there were considerable side effects with systemic delivery that, again, can be averted via intraventricular delivery. Accordingly, it would be desirable and advantageous to treat traumatic brain injuries and/or pain with GABA agonists without the side-effects and disadvantages described above. Furthermore, combining either intrathecal or intraventricular administration of gamma-aminobutyramide, derivatives thereof, and/or a drug or compound which yields gamma-aminobutyramide as an intermediate, metabolite or a by-product, with an implantable pump to provide constant delivery of the drug will provide anti-spasticity, anti-convulsive, and anti-epileptic efficacy.

SUMMARY OF THE INVENTION

According to the subject invention, there is disclosed a method for treating a patient/subject having a neuronal disorder or injury such as spastic disorder, a convulsive disorder, tardive dyskinesia, pain or epilepsy which includes administering to the subject having any one of these conditions a therapeutically effective amount of the compound gamma-aminobutyramide, analogs, substituted forms, derivatives, the pharmaceutically acceptable salts, esters, amides, and prodrugs thereof, and/or drugs or compounds which yield gamma-aminobutyramide as an intermediate, metabolite, or by-product.

BRIEF DESCRIPTION OF THE DRAWING

The following detailed description is best understood with reference to the following drawing in which.

DETAILED DESCRIPTION OF THE INVENTION

Figure 1:
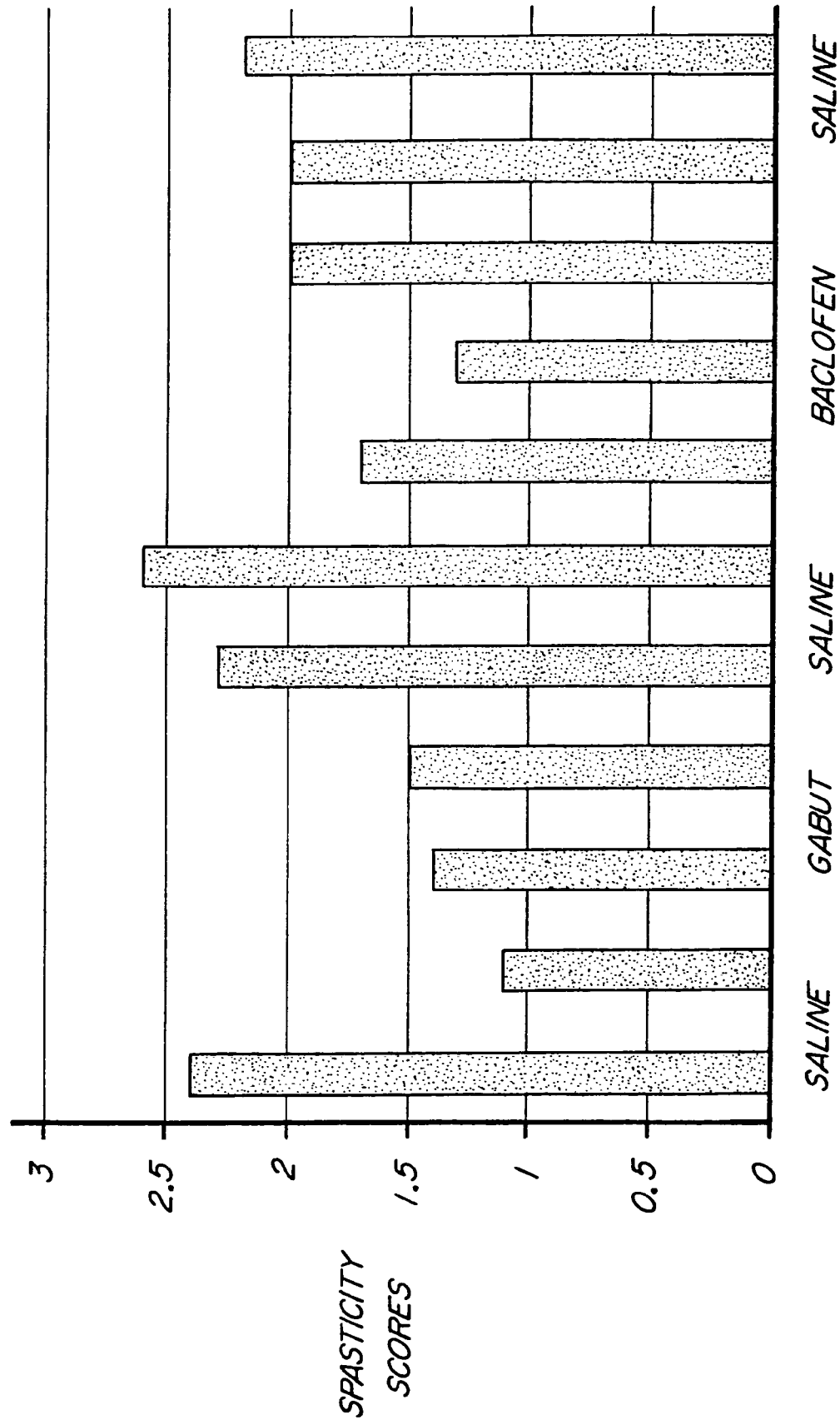
FIG. 1 is a graph illustrating the effects of various compounds on the spasticity levels of test animals wherein the compounds are normal saline (NS), GABAmide, and baclofen.

The present invention provides a method for treating neuronal conditions or disorders often associated with traumatic brain injury, including dystonia/spasticity, spastic disorders, convulsive disorders, tardive dyskinesia, pain or epilepsy by intrathecally or intraventricularly administering to a patient or subject having dystonia/spasticity, a spastic disorder, a convulsive disorder, pain or epilepsy a therapeutically effective amount of the compound gamma-aminobutyramide, analogs, substituted forms, derivatives, the pharmaceutically acceptable salts, esters, amides, and prodrugs thereof, and/or any compound or drug which, after being administered to the subject, yields gamma-aminobutyramide as an intermediate, metabolite, or a by-product.

The terms "patient" and "subject" mean all animals including humans. Examples of patients or subjects include humans, cows, dogs, cats, goats, sheep, and pigs.

The term "substituted" means that the base organic radical has one or more substituents.

The term "solubility products" means those compounds or compositions formed when a compound is disposed in a solvent.

Those skilled in the art are easily able to identify patients or subjects having dystonia/spasticity, spastic disorders, convulsive disorders, and epilepsy. For example, patients who have sustained traumatic brain injury induced dystonia/spasticity.

A therapeutically effective amount is an amount of gamma-aminobutyramide, analogs, substituted forms, derivatives, the pharmaceutically acceptable salts, esters, amides, and prodrugs thereof, or a drug or compound which yields gamma-aminobutyramide as an intermediate, metabolite, or a by-product that when administered to a patient or subject, ameliorates a symptom of the condition or disorder.

The compounds of the present invention can be administered to a patient either alone or as part of a pharmaceutical composition. The compositions can be administered to patients either intrathecally or intraventricularly.

Compositions suitable for intrathecal or intraventricular delivery may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyloleate. Proper fluidity can be maintained, for example, by the use of a coating such as lecithin, by the maintenance of the required particle size in the case of dispersions, and by the use of surfactants.

In a preferred embodiment, the compound administered to a patient or subject is the gamma-aminobutyramide, a solubility product obtained by dissolving PROGABIDE in a solvent thereby generating gamma-aminobutyramide and an insoluble ketone. The insoluble ketone (4-chlorophenyl-5-fluoro-2-hydroxyphenylmethanone) is subsequently removed by filtration leaving the pure, stable gamma-aminobutyramide. This compound is significantly more stable and has a longer half-life than PROGABIDE and, consequently, is stable enough to be either intrathecally and/or parenterally administered to the patient or subject.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Barge et al., "Pharmaceutical Salts," *J. Pharm. Sci.*, 1977, 66:1-19 which is incorporated herein by reference.)

Examples of pharmaceutically acceptable, non-toxic esters of the compounds of this invention include $C_1$-$C_6$ alkyl esters wherein the alkyl group is a straight or branched chain. Acceptable esters also include $C_1$-$C_7$ cycloalkyl esters as well as arylalkyl esters such as, but not limited to benzyl. $C_1$-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$-$C_3$ alkyl primary amines, and $C_1$-$C_2$ dialkyl secondary amines are preferred. Amides of the compounds of the invention may be prepared according to conventional methods.

The term "prodrug" refers to compounds that are rapidly transformed in vivo to yield the parent compounds of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can be administered to a patient at dosage levels in the range of about 100 μg to about 2000 μg per day. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The gamma-aminobutyramide, its analogs, substituted forms, derivatives, pharmaceutically acceptable salts, esters, amides, and prodrugs thereof, and/or compounds or drugs which yield gamma-aminobutyramide as an intermediate, metabolite, or a by-product, can be intrathecally or intraventricularly administered utilizing an intraspinal catheter. The intraspinal catheter is disposed within the spinal subarachnoid space in the thoracolumbar and sacral spinal regions. Since intrathecally delivered drugs can quickly cross out of or pass out of the intrathecal space to the spinal cord, in those patients with dystonia/spasticity involvement of the upper extremities, the medical provider inserting the catheter may wish to insert the intraspinal catheter more cephalid. Meythaler et al., *Perspectives in Neurosurg.* 1996; 7(2):99-107. A similar effect has been shown for intrathecal baclofen where the catheter was threaded more cephalid than the T-10 level which was found to improve sustained response in the upper extremity tone. Meythaler et al., *J. NeuroSurgery* 1997; 87:415-9; Meythaler et al., *Am J. Phys. Med. Rehabil.* 1998; 77-173.

As stated above, both the intrathecal and intraventricular administration of the gamma-aminobutyramide compound, analogs, substituted forms, derivatives, pharmaceutically acceptable salts, esters, amides, and prodrugs thereof, or the compounds or the drugs which yield gamma-aminobutyramide as an intermediate, a metabolite, or a by-product can be supported utilizing an implantable pump.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

The 4-[[(4-chlorophenyl)-(5-fluoro-2-hydroxyphenyl)methylene]amino]butanamide compound (PROGABIDE), analogs, substituted forms, derivatives, solubility products, and pharmaceutically acceptable salts, esters, amides, and prodrugs thereof can be obtained utilizing the synthesis described in U.S. Pat. No. 4,094,992.

EXPERIMENTAL

Use of Gamma-Aminobutyramide (GABAmide)

A study on the use GABAmide was performed to compare its effectiveness to reduce spasticity and assess toxicity via intrathecal delivery in a chronic spastic SCl rat model utilizing an implantable refillable pump.

Setting—University approved laboratory for animal testing and research.

Subjects—Twenty Sprague Dawley rats with severe spinal cord injury and spasticity, which were more than ten weeks from initial weight, drop injury. Five animals were selected that exhibited the highest degree of spasticity during the six-week observation period. The rats were implanted using the 2 French Fogarty balloon catheter attached to a refillable 1 cc. Pumps (ESOX Minneapolis Minn.) placed surgically in the subcutaneously between the shoulder blades one week earlier that had been effectively delivering preservative free normal saline. The ESOX pump flowed at a rate of 60 μl per day. The pump initially contained saline solution and the animals were again tested several days after pump placement for spasticity.

Design—Rats were randomized to a blinded three-arm study utilizing GABAmide, baclofen and placebo in a cross over design. The pump has the advantage that the solution in the pump can be changed so that drugs can be evaluated. GABAmide was placed in the pumps and the animals were evaluated at the times specified below.

Main Outcome Measures—Rats were tested weekly for levels of spasticity:

4) spasms spontaneously occur over a four minute observation period 3) spasms with light touch of the foot 2) spasms with passive movement of the foot and leg by extending the leg 1) spasms with painful stimulation—extend leg and pinch foot 0) no spasms inducible This scale was adapted for use in animals from the Ashworth score (Albright et al., *Intrathecal baclofen therapy for spasticity of cerebral origin: Patient selection guidelines* 1997), which has been utilized so frequently in human trials and in the clinical management of intrathecal baclofen. Meythaler et al., *Arch. Phys. Med. Rehabil.* 1999; 80:13-9; Agmo et al., *Pharinacol Biochem Behavior* 1998; 59:239-47; Jones et al., *Pharmcol Biochem Behavior* 1998; 59:319-26; Mondrup et al., *Acta Neurol Scand.* 1984; 69:191-9; Rudick et al., *Arch Neurol.* 1987; 44:1033-6; Bergmann et al., *Clin. Neuropharcol.* 1985; 8:13-26; Polasek et al., *Epilepsy Research* 1996; 25:177-84; Kulinskii et al., *Eksperimntalnaia I Klinicheskaia Farmakologiia* 1997; 60:56-8; Young et al., *New Eng. J. Med.* 1981; 304:28-33; Knuttson et al., *J. Neurol. Sci.* 1974; 23:473-484; Muller et al., *Local-spinal therapy of spasticity* 1988, 223-226. It is a similar five point ordinal scale. Rats were also assessed for functional changes utilizing the BBB scoring system for motor function and for their ability to walk a series of balance beams without falling that started at 7.7 cm. and decreased in 1 cm increments to 1.7 cm. in diameter (the smallest a normal rat can easily and reliably cross). A person who was unaware of the type of drug delivered or the expected effects of the drug performed all of the behavioral testing. Similar levels of spasticity were observed following the placement of the pump. Differences over times were assessed via descriptive statistics, Friedman's analysis, Wilcoxon signed-rank, for nonparametric data (spasticity, BBB score and beam walking).

Results—After six days of treatment the five rats with 5 micrograms per day of intrathecal GABAmide the mean spasticity score decreased from 2.4 SD+0.7 to 1.5 SD+0.5 (p=0.006, Friedman's). The maximal decrease with the GABAmide was at day two when the tone decreased to 1.1 SD+0.9 (Wilcoxon signed rank) before there was accommodation at day six where the effect on tone was still significant (p=0.0117, Wilcoxon signed rank). Three of the same rats were treated with intrathecal baclofen at a dose of 15 micrograms per day. The intrathecal baclofen also decreased tone after five days from a mean of 2.6 SD+0.7 to 2.0 SD+0 (p=0.0256, Friedman's). The maximal decrease with intrathecal baclofen was at day three when the tone decreased to 1.3 SD+0.5 (p=0.0431, Wilcoxon signed rank) but again there was accommodation at day five which was greater than with the GABAmide and approached statistical significance (p=0.0679, Wilcoxon signed rank). There were not statistical changes between the washout periods with the normal saline (NS) throughout the study (p>0.05, Wilcoxon signed rank) (See FIG. 1). There was not statistically significant change in the BBB score nor with beam walking with the GABAmide throughout the study. There was a decrease in the BBB score from 5.2 SD+4.1 to 2.7 SD+4.1 when the peak effect on spasticity was noted (p=0.0431, Wilcoxon signed rank). It was not significant at day five of treatment. Beam walking decreased from a mean of 5.2 cm. to 2.7 cm on the baclofen at day three (p=0.01, Friedman's). However, it recovered to 6.0 cm. at day five of treatment with baclofen.

Conclusion—Intrathecally GAMAmide is capable of reducing the spasticity in the rat model. Its lack of effect on other behavioral tests may be a reflection on its efficacy. The dosage required to reduce spasticity because it effects both GABA-A as well as GABA-B receptors may not be such as to have such a negative impact on other behavioral tests. It appears to be well tolerated for periods of time longer than those reported in the preclinical trials of baclofen. It also appears that GABAmide has less accommodation to spasticity than baclofen.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents or publications mentioned in the specification are indicative of the levels of those skilled in the art to which the invention pertains. These patents and publications are herein incorporated by reference to the same extent as if each individual publication was specifically and individually indicated to be incorporated by reference.

The invention claimed is:

1. A method of treating spastic disorders, said method comprising administering to a subject having a spastic disorder a therapeutically effective amount of a compound consisting of gamma-aminobutyramide, or a pharmaceutically acceptable salt thereof and wherein said administering does not generate 4-chlorophyenyl-5-fluoro-2-hydroxyphenylmethanone.

2. A method according to claim 1, wherein said administering step further comprises intrathecally delivering the compound.

3. A method according to claim 2, wherein said intrathecal delivering step comprises delivering the compound through a spinal catheter inserted in a substantially cephalid spinal location.

4. A method according to claim 1, wherein said administering step further comprises intraventricularly delivering the compound.

5. A method according to claim 1, wherein said administering step further comprises delivering the compound to the subject through an implantable pump.

6. A method according to claim 1, wherein said administering step further comprises delivering the compound to the subject through a spinal catheter.

7. A method according to claim 1, wherein the spastic disorder is spastic hypertonia.

8. A method according to claim 1, wherein the spastic disorder is dystonia.

9. A method according to claim 1, wherein the spasticity or spastic disorder is caused by traumatic brain injury.

10. A method for treating convulsions, said method comprising administering to a subject either having convulsions or predisposed to convulsions a therapeutically effective amount of a compound consisting of gamma-aminobutyramide, or a pharmaceutically acceptable salt thereof and wherein said administering does not generate 4-chlorophyenyl-5-fluoro-2-hydroxyphenylmethanone.

11. A method according to claim 10, wherein said administering step further comprises intrathecally delivering the compound.

12. A method according to claim 11, wherein said intrathecal delivering step comprises delivering the compound through a spinal catheter inserted in a substantially cephalid spinal location.

13. A method according to claim 10, wherein said administering step further comprises intraventricularly delivering the compound.

14. A method according to claim 10, wherein said administering step further comprises delivering the compound to the subject through an implantable pump.

15. A method according to claim 10, wherein said administering step further comprises delivering the compound to the subject through a catheter.

16. A method for treating epilepsy, said method comprising intraventricularly administering a therapeutically effective amount of a compound consisting of gamma-aminobutyramide, or a pharmaceutically acceptable salt thereof and wherein said administering does not generate 4-chlorophyenyl-5-fluoro-2-hydroxyphenylmethanone.

17. A method of treating idiopathic dystonia or torsional dystonia, said method comprising administering to a subject having idiopathic dystonia or torsional dystonia a therapeutically effective amount of a compound consisting of gamma-aminobutyramide and wherein said administering does not generate 4-chlorophyenyl-5-fluoro-2-hydroxyphenylmethanone.

* * * * *